(12) United States Patent
Faber et al.

(10) Patent No.: US 8,596,537 B2
(45) Date of Patent: Dec. 3, 2013

(54) ANESTHESIA SYSTEM

(75) Inventors: Sönke Faber, Stockelsdorf (DE); Wolfgang Falb, Groß Sarau (DE); Michael Heidschmidt, Lübeck (DE); Sven Heyer, Lübeck (DE); Götz Kullik, Lübeck (DE); Frank Mecklenburg, Lübeck (DE); Martin Meyer, Lübeck (DE); Gerd Peter, Lübeck (DE); Klaus Radomski, Lübeck (DE); Hartmut Stark, Stockelsdorf (DE)

(73) Assignee: Dräger Medical GmbH, Lübeck (DE)

( * ) Notice: Subject to any disclaimer, the term of this patent is extended or adjusted under 35 U.S.C. 154(b) by 535 days.

(21) Appl. No.: 12/830,726

(22) Filed: Jul. 6, 2010

(65) Prior Publication Data
US 2011/0031313 A1 Feb. 10, 2011

(30) Foreign Application Priority Data
Aug. 5, 2009 (EP) .................................... 09167232

(51) Int. Cl.
*G06K 7/10* (2006.01)
(52) U.S. Cl.
USPC ..................................... 235/462.01; 235/454
(58) Field of Classification Search
USPC .......... 235/454, 462.01; 250/206, 338.1, 372; 128/203.12
See application file for complete search history.

(56) References Cited

U.S. PATENT DOCUMENTS

| 5,051,729 | A | * | 9/1991 | Gray .............................. 340/626 |
| 5,293,865 | A | * | 3/1994 | Altner et al. ............. 128/203.12 |
| 5,651,775 | A | * | 7/1997 | Walker et al. .................. 604/207 |
| 8,058,635 | B2 | * | 11/2011 | Cierullies et al. ............. 250/573 |

FOREIGN PATENT DOCUMENTS

| DE | 296 14 491 U1 | 12/1996 |
| DE | 102007014838 | 3/2008 |
| EP | 0 338 518 B1 | 10/1989 |
| EP | 1 563 859 A1 | 8/2005 |

\* cited by examiner

*Primary Examiner* — Daniel Hess
*Assistant Examiner* — Rafferty Kelly
(74) *Attorney, Agent, or Firm* — McGlew and Tuttle, P.C.

(57) ABSTRACT

An anesthesia system (1) is provided with an anesthesia apparatus (2), at least one anesthetic dispenser (3) and at least one parameter detection device (7) for detecting at least one parameter of the at least one anesthetic dispenser (3) at the anesthesia apparatus (2). The parameter detection device (7) is provided with an apparatus interface unit (10) with at least one camera (17) at the anesthesia apparatus (2) and with a dispenser interface unit (11) with at least one image pattern (16) at the at least one anesthetic dispenser (3). The at least one image pattern (16) can be detected by the camera (17), and the dispenser interface unit (11) is a passive dispenser interface unit (11).

19 Claims, 3 Drawing Sheets

ANESTHESIA SYSTEM

CROSS REFERENCE TO RELATED APPLICATIONS

This application claims the benefit of priority under 35 U.S.C. §119 of European Patent Application EP 09 167 232.5 filed Aug. 5, 2009, the entire contents of which are incorporated herein by reference.

FIELD OF THE INVENTION

The present invention pertains to an anesthesia system with an anesthesia apparatus with an anesthetic dispenser.

BACKGROUND OF THE INVENTION

Predominantly anesthetics in the vapor form are used in medical engineering for the anesthesia of patients, especially in surgical procedures. An anesthesia system with an anesthesia apparatus and with an anesthetic dispenser are necessary for this. The anesthetic is contained in the anesthetic dispenser with an anesthetic reservoir. An energy-consuming electric heating means is used in the anesthetic dispenser in active anesthetic dispensers, among other things, for controlling the quantity of anesthetic that is fed into the breathing gas. No energy-consuming heating means is present in the anesthetic dispenser in the case of passive anesthetic dispensers. Passive anesthetic dispensers can be manufactured at a lower cost.

EP 0 338 518 B1 shows an anesthesia means with an anesthetic evaporator, from which the anesthetic can be fed into the setting device, from which dispensed quantities of anesthetic can be released to an anesthesia apparatus.

DE 10 2007 014 838 B3 shows a class-forming anesthesia system comprising an anesthesia apparatus, an anesthetic dispenser with an anesthetic reservoir, at least one dispensing parameter detection means and with a contactless interface between the anesthesia apparatus and the anesthetic dispenser for transmitting data, especially the dispensing parameters, and supplying the at least one dispensing parameter detection means with energy, wherein the data and the energy transmission are brought about by electromagnetic field forces. The transmission of data and energy by electromagnetic field forces is disadvantageously complicated. Furthermore, mutual interference may occur between the anesthetic dispensers with the respective interfaces because of the electromagnetic field forces in case of a plurality of anesthetic dispensers.

SUMMARY OF THE INVENTION

The object of the present invention is to make available an anesthesia system in which an anesthetic filling level in an anesthetic dispenser and additional parameters of the anesthetic dispenser can be determined and transmitted in a simple manner. Furthermore, the anesthesia system shall be technically simple and reliable in operation.

According to the invention, an anesthesia system is provided comprising an anesthesia apparatus with an anesthetic dispenser. A parameter detection means is provided for detecting at least one parameter of the at least one anesthetic dispenser at the anesthesia apparatus. The parameter detection means is provided with an apparatus interface unit with at least one camera at the anesthesia apparatus and with a dispenser interface unit with at least one image pattern at the at least one anesthetic dispenser. The at least one image pattern can be detected by the camera and the dispenser interface unit is a passive dispenser interface unit.

The pneumatic connection between the at least one anesthetic dispenser and the anesthesia apparatus is preferably established with at least one pneumatic interface. A passive dispensing interface unit consumes no energy or auxiliary energy during or for the operation. As a result, no means for transmitting energy, especially electric energy from the anesthesia apparatus to the anesthetic dispenser are advantageously needed in the anesthesia system in order to supply the dispensing interface unit and/or the means with energy. Even though energy, for example, light energy, can be transmitted from the anesthesia apparatus to the anesthetic dispenser, this energy, for example, light energy, is not needed to operate the at least one dispensing interface unit, but it is used to detect parameters of the anesthetic dispenser by means of the light. The energy is thus only a parameter detection means, especially a direct and non-modified parameter detection means.

In another embodiment, the transmission of data from the at least one anesthetic dispenser to the anesthesia apparatus can be performed by means of infrared radiation or visible light or UV radiation.

Infrared radiation has a wavelength between 780 nm and 1,000,000 nm and especially between 780 nm and 5,000 nm. Visible light has a wavelength between 380 nm and 780 nm. UV radiation has a wavelength between 1 nm and 380 nm.

The camera operates in the visible spectral range or infrared range or in the UV range.

In one variant, the at least one dispensing interface unit comprises a code. The code is advantageously an optical code.

In another embodiment, the optical code is a bar code and/or a two-dimensional code, e.g., a data matrix code. The bar code is, for example, a chain code with a one-piece bar code of 12 or 13 bit data. The code may, moreover, be provided with a Hamming distance greater than 2, so that individual reading errors may also possibly be corrected as a result.

Reading errors, for example, those resulting from contamination, can be compensated as a result.

In particular, the at least one apparatus interface unit comprises an optical encoder unit for optically detecting the optical code of the dispensing interface unit. The optical encoder unit is preferably composed of light-emitting diode (LED) and a camera. As an alternative, a lamp may also be provided instead of the LED. The camera may be designed as a Complementary Metal-Oxide Semiconductor (CMOS) chip camera.

In another variant, an anesthetic filling level in the anesthetic dispenser can be determined at the anesthesia apparatus with the at least one parameter detection means.

In another embodiment, the filling level can be determined by the means for detecting the anesthetic filling level by means of a change in the refractive index difference, so that a different refractive index and hence a different radiation intensity, especially light intensity occurs at the receiver in case of a different filling level. The detection of the filling level by means of a change in the refractive index at an optical interface does not represent an energy-consuming or energy-converting means for the operation of the means. The electromagnetic radiation is not consumed to operate the means.

In particular, electromagnetic radiation, especially light, can be introduced by the optical encoder of the apparatus interface unit into a guide, especially a fiber-optic light guide, of the means for detecting the filling level by the optical encoder of the apparatus interface unit. The electromagnetic radiation introduced, especially light, can be reflected at an optical interface as a function of the anesthetic filling level, and the at least one image pattern is generated from the difference of the radiation intensity of the electromagnetic radiation. The filling level can be detected by the camera on the basis of the radiation intensity, especially the light intensity, of the reflected electromagnetic radiation, especially light. For example, a rod made of glass or a plastic or even one or more glass fibers may be used as guides for light or electromagnetic radiation.

In another embodiment, a position, especially an angular position, of an adjusting means, especially of a handwheel of the anesthetic dispenser at the anesthesia apparatus, can be detected with the at least one parameter detection means. The adjusting means comprises a code, which can be read as an image pattern by the camera of the at least one apparatus interface unit. The quantity of anesthetic, which is fed to the breathing gas sent through the anesthetic dispenser, is controlled and/or regulated by means of the adjusting means. The code at the adjusting means is designed such that the code contains data from which the position of the adjusting means can be determined. The code of the adjusting means is an optical code here, for example, a bar code. A two-dimensional code or a color code or an analog code by means of detection of the width of a wedge, may be provided as an alternative as well.

In an additional embodiment, data pertaining to the type of the anesthetic dispenser and/or a part number of the anesthetic dispenser and/or a serial number of the anesthetic dispenser and/or the type of the anesthetic can be transmitted by the interface and, in particular, these data are stored in the at least one image pattern of the dispensing interface unit.

In general, the type of anesthetic appears from the type of the anesthetic dispenser, because only one certain type of anesthetic dispenser is used for each type of anesthetic. As a result, the anesthesia apparatus receives the information on the type of the anesthetic being used. The version or the design of the anesthetic dispenser appears from the part number. As a result, the anesthesia apparatus receives data concerning the design and technical embodiment of the anesthetic dispenser.

The serial number of the anesthetic dispenser makes it possible to identify the anesthetic dispenser. The anesthetic dispensers are used at various anesthesia apparatus in a hospital. A certain anesthetic dispenser can thus be located and identified with a network within the hospital in case of a necessary maintenance of an anesthetic dispenser, so that there is no need as a result for a costly search for a maintenance or repair of the anesthetic dispensers. Furthermore, the date of manufacture of the anesthetic dispenser may be directly or indirectly contained in a serial number of the anesthetic dispenser. As an alternative hereto, the date of manufacture may be stored separately.

In another embodiment, the anesthesia system comprises at least two anesthetic dispensers and/or the anesthesia apparatus is designed such that at least two anesthetic dispensers can be connected, so that, for example, two pneumatic interfaces, two mechanical fastening means and two optical encoders are present. It is necessary in this anesthesia system that devices that prevent the simultaneous use of two anesthetic dispensers be present to prevent two different anesthetics to be supplied to the patient. This may be embodied either by a warning means being present in case of simultaneous operation of two anesthetic dispensers or simultaneous operation of two anesthetic dispensers is ruled out based on design and technical implementation.

For example, halothane, isoflurane, sevoflurane and enflurane are used as anesthetics in a passive anesthetic dispenser, which has no electric heating means for heating the anesthetic. For example, desflurane is used as the anesthetic in case of active anesthetic dispensers with an electric heater for heating or tempering the anesthetic to a certain temperature.

An exemplary embodiment of the present invention will be described in more detail below with reference to the drawings attached. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
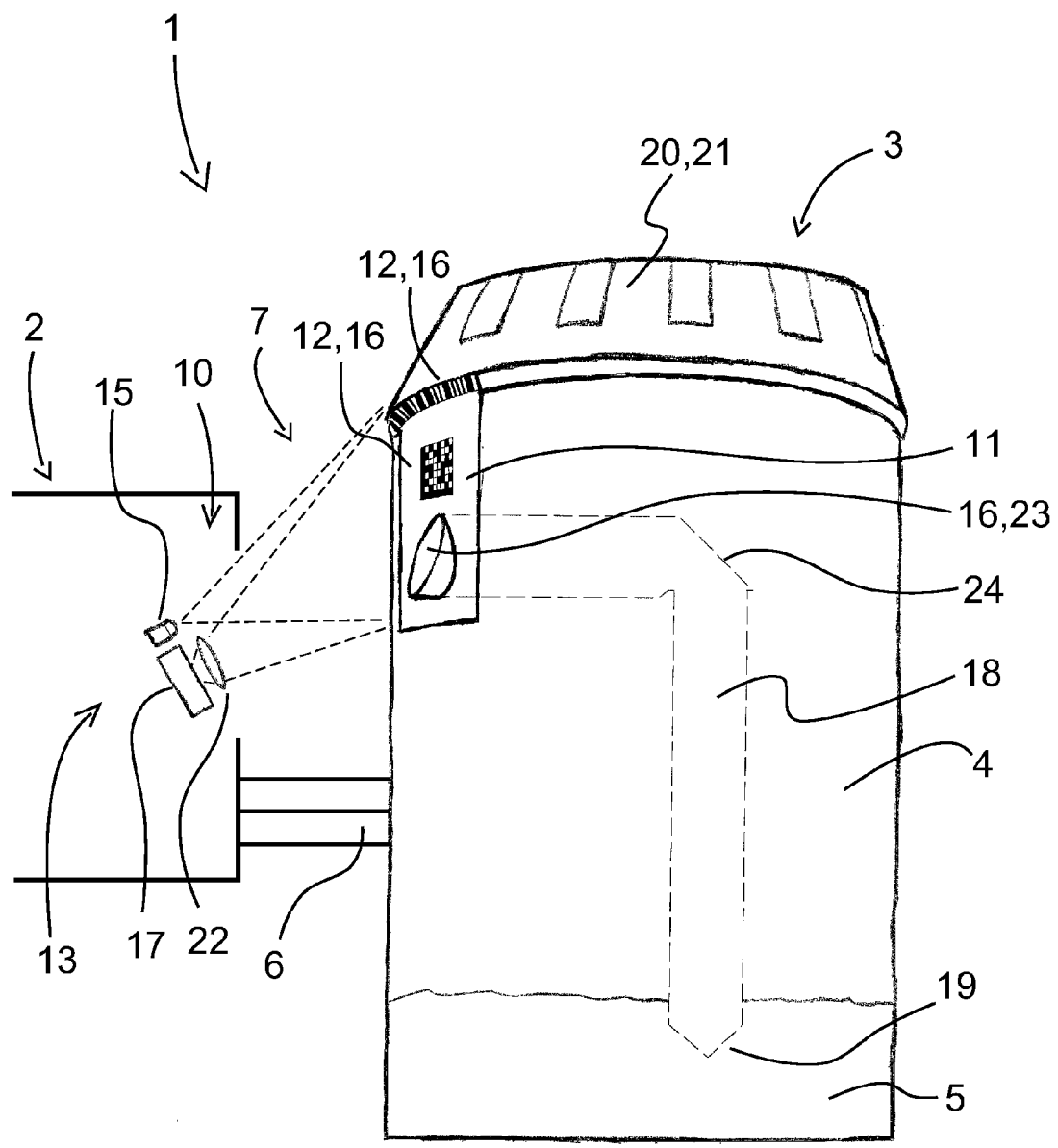
FIG. 1 is a simplified longitudinal view of a first embodiment of the anesthesia system according to the present invention.

Referring to the drawings in particular, FIG. 1 shows an anesthesia system 1 with an anesthesia apparatus 2 and an anesthetic dispenser 3. The anesthesia system 1 is used to enrich a respirating gas with anesthetic 5 during the artificial respiration of patients, especially during surgical procedures, and to supply it to the patient. The anesthetic dispenser 3 is attached to the anesthesia apparatus 2 by means of mechanical fastening means. The mechanical fastening means are not shown in FIG. 1. An anesthetic reservoir 4 containing an anesthetic 5 is present in the anesthetic dispenser 3. A pneumatic interface 6 is used for the pneumatic connection of the anesthetic dispenser 3 with the anesthesia apparatus 2. Respirating gas can thus be sent from the anesthesia apparatus 2 through the anesthetic reservoir 4 and subsequently back into the anesthesia apparatus 2. The respirating gas is enriched with anesthetic 5 during the passage of the respirating gas through the anesthetic reservoir 4. The anesthetic 5 now evaporates or vaporizes in the anesthetic reservoir 4.

An adjusting means 20 designed as a handwheel 21 is used to control the quantity of anesthetic vapor 5 to be fed to the respirating gas. The handwheel 21 can be moved manually (by hand) to control the quantity of anesthetic 5 to be fed. The anesthetic dispenser 3 has a bypass duct (not shown), through which the respirating gas sent through the anesthetic dispenser 3 can be sent past the anesthetic reservoir 4. The quantity of respirating gas, which flows through this bypass duct, can be set or controlled by means of handwheel 21. The larger the quantity of respirating gas sent through the bypass duct, the smaller is the quantity of respirating gas flowing through the anesthetic reservoir 4 and the smaller is the quantity of anesthetic 5 fed into the respirating gas in the anesthetic dispenser 3 and vice versa (not shown).

The anesthetic dispenser 3 is a passive anesthetic dispenser 3 and therefore does not have an electric heating means for controlling and/or regulating the temperature of the anesthetic 5. Therefore, there also is no electric connection between the anesthesia apparatus 2 and the anesthetic dispenser 3 for supplying an electric heating means, which is not present.

The anesthesia system 1 has a parameter detection means 7 for transmitting and detecting data from the anesthetic dispenser 3 to the anesthesia apparatus 2. The parameter detection means 7 comprises an apparatus interface unit 10 and a dispenser interface unit 11. The apparatus interface unit 10 is arranged at the anesthesia apparatus 2 and the dispenser interface unit 11 is arranged at the anesthetic dispenser 3. The apparatus interface unit 10 comprises at least one camera 17. Furthermore, an analysis unit (not shown), which performs the further processing of the signals of camera 17, is arranged downstream of camera 17. The dispenser interface unit 11 comprises at least one image pattern 16.

The essentially plate-shaped handwheel 21 has an annular optical code 12 as a bar code on its entire outer edge. The optical code 12 represents the image pattern 16 of the dispenser interface unit 11. An optical encoder 13 is arranged at the anesthesia apparatus 2 in the area of this optical code 12 of the handwheel 21. The optical encoder 13 comprises an LED 15 and a camera 17. The LED 15 emits light, which is radiated to the image pattern 16 comprising the optical code 12 on the outside of the handwheel 21. The camera 17 can detect the code 12 of the image pattern 16 from the light reflected by the image pattern 16 and the analysis unit in the anesthesia apparatus 2 can determine the position of handwheel 21. Data on the position, especially angular position of the handwheel 21, can thus be sent to the anesthesia apparatus 2. The anesthesia apparatus 2 can thus receive data on the anesthetic concentration in the respirating gas sent through the anesthetic dispenser 3. The optical encoder 13 represents, furthermore, the apparatus interface unit 10.

Another image pattern 16 is arranged under the handwheel 21. The image pattern 16 is designed as an optical code 12. The optical code 12 is arranged as a data matrix code. The data matrix code contains data concerning the type, part number and serial number of the anesthetic dispenser 3. The image pattern 16 of the optical code 12 can be detected by the optical encoder 13 at the anesthesia apparatus 2. Camera 17 detects the data stored in the image pattern 16 of the optical code 12.

The optical encoder 13 for detecting the angular position of the handwheel 21 by means of the corresponding image pattern 16 of the optical code 12 on the handwheel 21 is thus a parameter detection means 7 for detecting a position of an adjusting means 20 as a parameter of the anesthetic dispenser 3.

Figure 2:
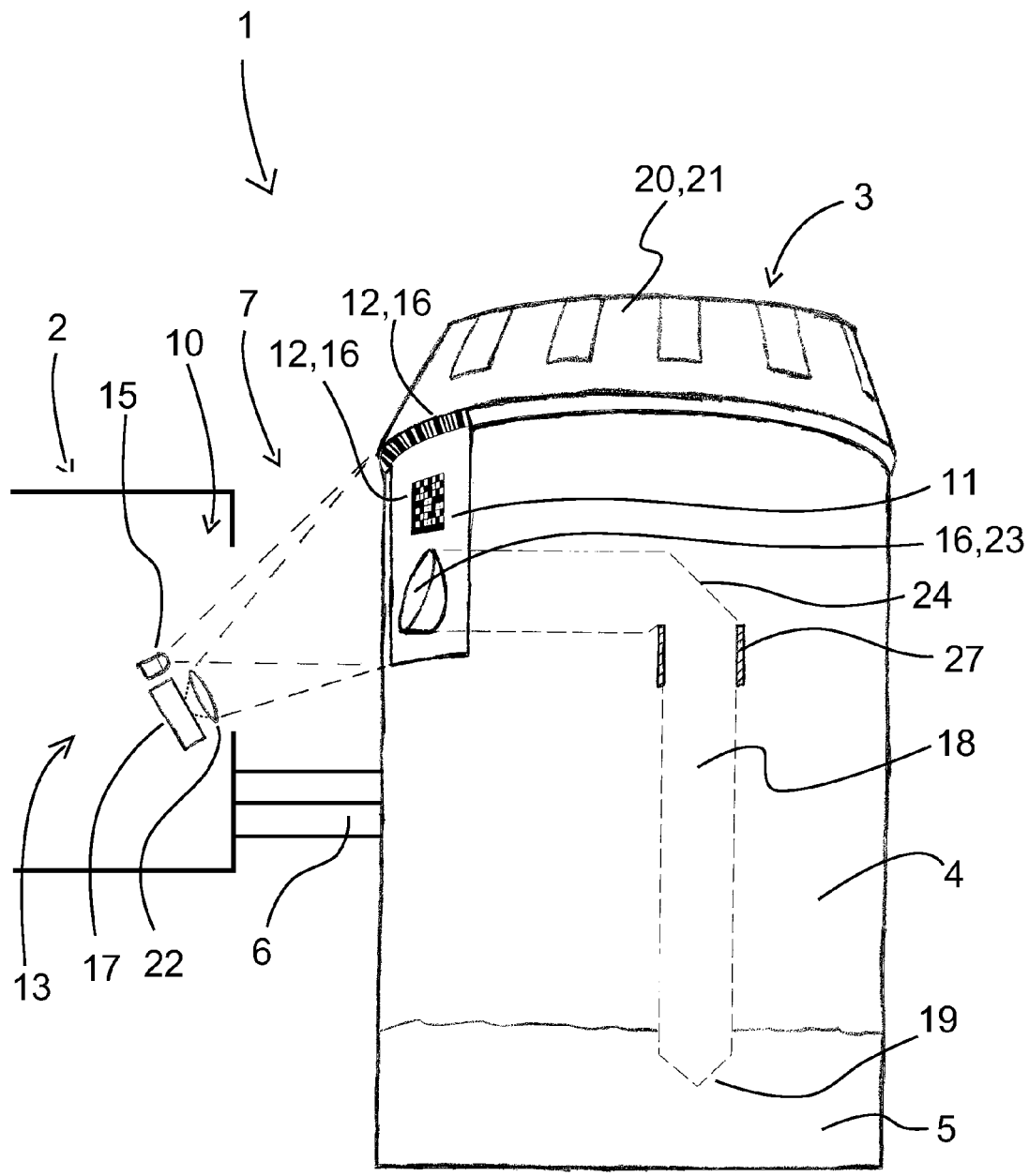
FIG. 2 is a simplified longitudinal view similar to FIG. 1 and showing a means for detecting the filling level of an anesthetic of the anesthesia system according to FIG. 1.
Figure 3:
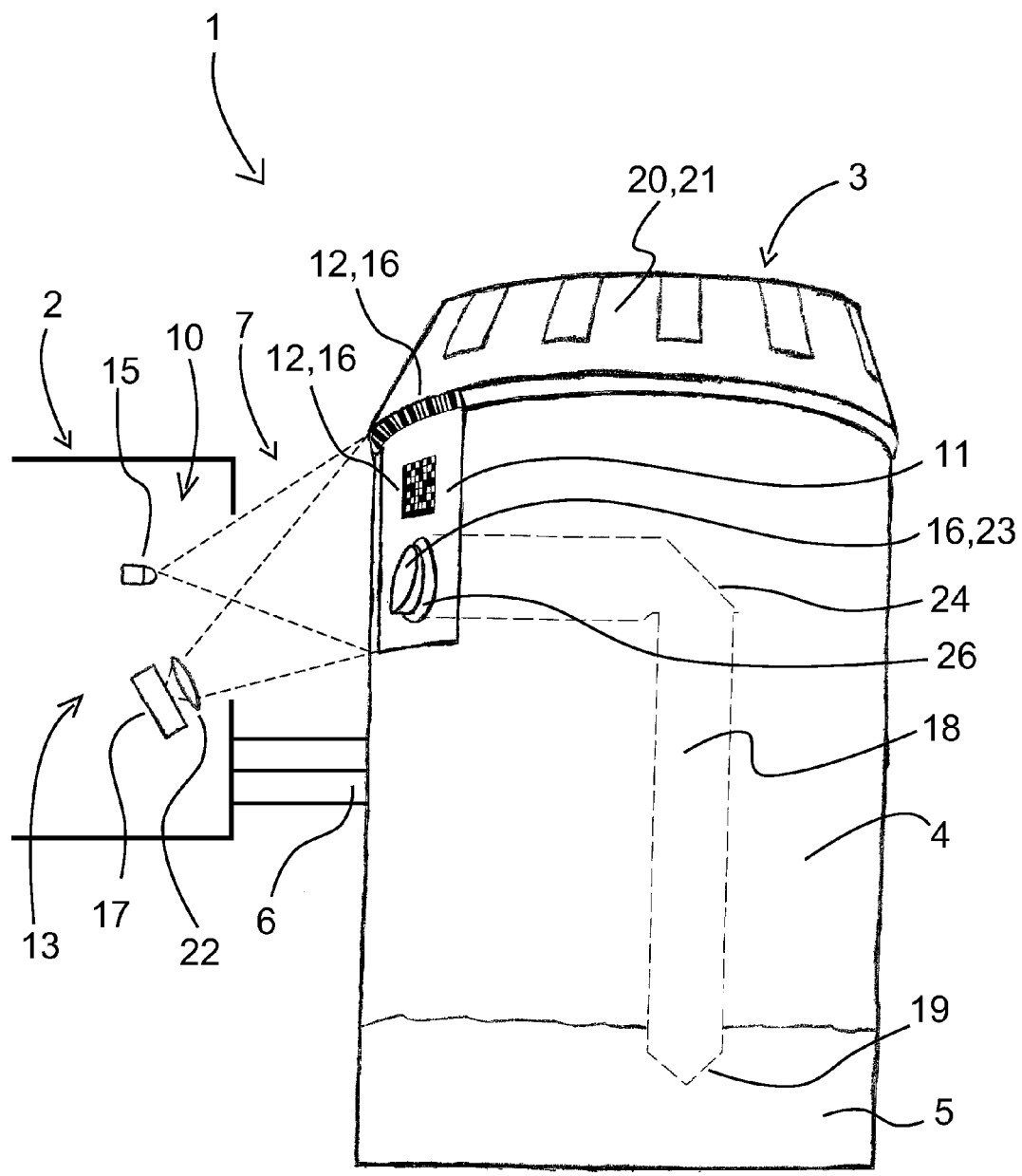
FIG. 3 is a simplified longitudinal view of a second embodiment of the anesthesia system according to the present invention.

The anesthesia system 1 is provided, furthermore, with a parameter detection means 7 for detecting the anesthetic 5 filling level in the anesthetic reservoir 4 (FIGS. 1, 2 and 3).

In a first embodiment, shown in FIG. 1, the light emitted by an LED 15 falls on an external coupling window 23 of a fiber-optic light guide 18 at the dispenser interface unit 11. The fiber-optic light guide 18 consists of glass or plastic. The fiber-optic light guide 18 is L-shaped and has an essentially horizontally and vertically directed bar. The light emitted by the LED 15 is coupled into the fiber-optic light guide 18 at the coupling window 23. This light, coupled into the horizontal bar of the fiber-optic light guide 18, is reflected at a reflection surface 24 of the fiber-optic light guide 18 and introduced as a result vertically downward into the vertical bar of the fiber-optic light guide 18. This vertically downwardly directed light reaches an optical interface 19. The optical interface 19 may be designed, for example, as a 90° cone. Depending on whether the optical interface 19 is immersed into the liquid anesthetic 5 or not, different refractive indices develop at the optical interface 19. If the optical interface 19 is not in the anesthetic 5, the light sent vertically downward to the interface 19 is reflected essentially completely as a total reflection at the optical interface 19 and is again sent vertically upward in the vertical bar of the fiber-optic light guide 19. This totally reflected light is subsequently reflected at the reflection surface 24 and is sent again horizontally back in the horizontal bar of the fiber-optic light guide 18 to the coupling window 23. This light, reflected totally at the optical interface, is sent downward in an oblique position at the coupling window 23 to a lens 22 based on the difference in the refractive index and subsequently to the camera 17. A different refractive index and hence a different radiation intensity of the light occur in case of a different anesthetic filling level, and the image pattern 16 is generated from the difference of the radiation intensity of the light. Camera 17 as a receiver of light can detect the image pattern 16 (the radiation intensity of this reflected light). If the optical interface is located in the liquid anesthetic, the difference in the refractive index of the optical interface 19 decreases to the extent that the total reflection angle is essentially exceeded and a majority of the electromagnetic radiation is uncoupled from the fiber-optic light guide 19. As a result, only a very small quantity of light is reflected at the optical interface, so that only a very low radiation intensity of reflected light is present at the camera 17. The anesthetic 5 filling level in the anesthetic reservoir 4 can thus be detected. In case of high radiation intensity of the light sent into camera 17, the anesthetic 5 in the anesthetic reservoir 4 is thus below the optical interface 19 of the fiber-optic light guide 18, i.e., only a very small residual quantity of anesthetic 5 is present in the anesthetic reservoir 4. In case of a low radiation intensity at the camera 17 when the LED is switched on, the anesthetic 5 liquid level in the anesthetic reservoir 4 is above the optical interface 19 of the fiber-optic light guide 18. These data on the filling level can be detected by camera 17, which is arranged at the anesthesia apparatus 2.

As an alternative, the coupling window 23 may be provided with a radially circumferentially extending collar 26, as is shown in FIG. 3. LED 15 is arranged in the longitudinal axis of the horizontal part of the fiber-optic light guide 18. Collar 26 makes it possible to couple in the light emitted by the LED 15.

In another variant of the means for detecting the filling level 7, the upper vertical part of the fiber-optic light guide 18 is surrounded by a sleeve 27 made of a reflecting material. A permanent ring can thus be generated in the image pattern 16 and hence in the field of vision area of camera 17, which marks the position of the vertical part of the fiber-optic light guide 18 in the field of vision area of camera 17. The detection area for the change in brightness can thus advantageously be set even in case of a completely filled anesthetic reservoir 4. Furthermore, the ability of the interface between the horizontal and vertical parts of the fiber-optic light guide 18 to function can be recognized on the basis of the light intensity of the ring.

Electromagnetic radiation is preferably emitted by the LED 15 as an infrared radiation invisible for humans, so that the optical detection of data is not visible. The coupling window 23 of the fiber-optic light guide 18 likewise represents the dispenser interface unit 11, because an image pattern 16 can be generated here analogously to an optical code 12 and data can thus be transmitted from the anesthetic dispenser to the anesthesia apparatus.

On the whole, considerable advantages are associated with the anesthesia system 1 according to the present invention. The transmission of data from the anesthetic dispenser 3 to the anesthesia apparatus 2 takes place simply and reliably by means of optical means. It is not necessary for the anesthetic dispenser 3 to be supplied with energy for operating a parameter detection means 7 of the anesthetic dispenser 3. The anesthetic dispenser 3 can thus have a simple design and be manufactured at a low cost, especially as a passive anesthetic dispenser 3.

While specific embodiments of the invention have been described in detail to illustrate the application of the principles of the invention, it will be understood that the invention may be embodied otherwise without departing from such principles.

LIST OF REFERENCE NUMBERS

1 Anesthesia system
2 Anesthesia apparatus
3 Anesthetic dispenser
4 Anesthetic reservoir
5 Anesthetic
6 Pneumatic interface
7 Parameter detection means
10 Apparatus interface unit
11 Dispenser interface unit
12 Optical code
13 Optical encoder
15 LED
16 Image pattern
17 Camera
18 Fiber-optic light guide
19 Optical interface
20 Adjusting means
21 Handwheel
22 Lens
23 Coupling window
24 Reflection surface
26 Collar
27 Sleeve

What is claimed is:

1. An anesthesia system comprising:
an anesthesia apparatus;
an anesthetic dispenser operatively connected to the anesthesia apparatus;
a parameter detection means for detecting at least one parameter of the anesthetic dispenser at the anesthesia apparatus;
an apparatus interface unit associated with the parameter detection means, the apparatus interface unit comprising a camera at the anesthesia apparatus, the camera having a single two dimensional field of vision area and providing a two dimensional signal; and
a dispenser interface unit associated with the parameter detection means, the dispenser interface unit having an image pattern at the anesthetic dispenser, wherein the image pattern is detected by the camera, the dispenser interface unit being a passive dispenser interface unit, wherein:
the image pattern does not change during operation of the anesthesia system and presents data relating to a predefined parameter of the anesthetic dispenser and the dispenser interface unit includes another image pattern at the anesthetic dispenser that does change during operation of the anesthesia system and presents data relating to a current state of the anesthetic dispenser based on a parameter that changes during operation of the anesthesia system;
the image pattern and the another image pattern are in the single two dimensional field of vision area and are both detected by the camera;
the apparatus interface unit further comprises a radiation source emitting at least one of infrared radiation, visible light and UV radiation at the image pattern and the another image pattern;
the camera operates in at least one of a visible spectral range, infrared range and UV range in coordination with the radiation source; and
the image pattern detection by the camera includes a transmission of data from the anesthetic dispenser to the anesthesia apparatus, the transmission of data being by means of infrared radiation or visible light or UV radiation.

2. An anesthesia system in accordance with claim 1, wherein the image pattern comprises data concerning at least one of a type of the anesthetic dispenser and a part number of the anesthetic dispenser and a serial number of the anesthetic dispenser and a type of the anesthetic in the anesthetic dispenser.

3. An anesthesia system in accordance with claim 1, wherein:
the image pattern is an optical code comprising at least one of a bar code, a two-dimensional code and a data matrix code; and
the apparatus interface unit comprises an optical encoder for optical detection of the optical code of the dispenser interface unit, the optical encoder comprising the radiation source and the camera.

4. An anesthesia system in accordance with claim 1, wherein the at least one parameter detection means includes an anesthetic filling level detector of the anesthetic dispenser at the anesthesia apparatus, the anesthetic filling level detector comprising an external coupling window defining the another image pattern at the anesthetic dispenser, that does change during operation of the anesthesia system and presents data relating to a current state of the anesthetic dispenser.

5. An anesthesia system in accordance with claim 4, wherein the anesthetic filling level detector detects an anesthetic filling level by determining a change in a ratio of refractive indices of electromagnetic radiation, wherein a different refractive index and a different radiation intensity of the electromagnetic radiation develops in case of a different filling level, wherein the image pattern is generated from a difference of the radiation intensity of the electromagnetic radiation.

6. An anesthesia system in accordance with claim 4, wherein:
the anesthetic filling level detector comprises a fiber-optic light guide with an optical interface comprising the external coupling window;
the apparatus interface unit further comprises a radiation source emitting radiation that is introduced into the fiber-optic light guide of the dispenser interface unit;
the light introduced is reflected at the optical interface as a function of the anesthetic filling level and provides the another image pattern, which is detected by the camera, and is generated by a radiation intensity of reflected light; and
the radiation intensity is an indicator of the anesthetic filling level in the anesthetic dispenser.

7. An anesthesia system in accordance with claim 6, wherein apart of the fiber-optic light guide is surrounded by a sleeve formed of reflecting material.

8. An anesthesia system in accordance with claim 1, wherein:
the anesthetic dispenser has an adjusting means for adjusting anesthetic dispensing; and the another image pattern at the anesthetic dispenser, that does change during operation of the anesthesia system and presents data relating to a current state of the anesthetic dispenser, comprises indica on the adjusting means that changes relative to the single field of vision area with a change in an adjustment position.

9. An anesthesia system comprising:
an anesthesia apparatus;
a pneumatic interface;
an anesthetic dispenser with anesthetic, the anesthetic dispenser being connected to and disconnectable from the anesthesia apparatus with a pneumatic connection provided between the anesthesia apparatus and the anesthetic dispenser by the pneumatic interface and with no electric connection between the anesthesia apparatus and the anesthetic dispenser and no electric connection to the anesthetic dispenser;
an apparatus interface unit provided with a camera at the anesthesia apparatus, the camera having a single two dimensional field of vision area directed at the anesthetic dispenser, the apparatus interface unit being a part of the anesthesia apparatus; and
a dispenser interface unit fixed to the anesthetic dispenser, the dispenser interface unit comprising:
an image providing a code presenting at least one of anesthetic dispenser type data, anesthetic dispenser part number data, anesthetic dispenser serial number data and type of anesthetic in the anesthetic dispenser data; and
another image pattern that changes during operation of the anesthesia system and presents data relating to a current state of the anesthetic dispenser wherein the image pattern and the another image pattern are in the single field of vision area.

10. An anesthesia system in accordance with claim 9, wherein the anesthetic dispenser includes an anesthetic filling level indicator fixed to the anesthesia apparatus, the anesthetic filling level indicator comprising an external coupling window defining the another image pattern at the anesthetic dispenser, that changes during operation of the anesthesia system and presents data relating to a current state of the anesthetic dispenser.

11. An anesthesia system in accordance with claim 10, wherein the anesthetic filling level detector indicates a filling level by changing a reflected radiation intensity with the reflected radiation intensity at the external coupling window changing in case of different filling levels, wherein the image pattern changes during operation of the anesthesia at least based on a change between the different filling levels.

12. An anesthesia system in accordance with claim 11, wherein:
the apparatus interface unit further comprises a radiation source emitting at least one of infrared radiation, visible light and UV radiation at the image pattern and the another image pattern; and
the camera operates in at least one of a visible spectral range, infrared range and UV range in coordination with the radiation source.

13. An anesthesia system in accordance with claim 10, wherein:
the anesthetic dispenser further comprises an adjusting handwheel for adjusting a quantity of anesthetic fed by the anesthetic dispenser;
the dispenser interface unit further comprises a further image pattern at the anesthetic dispenser, that changes during operation of the anesthesia system and presents data relating to a current state of the anesthetic dispenser, the further image pattern comprising indica on the adjusting handwheel that changes relative to the single field of vision area with a change in an adjustment position; and
the further image pattern is in the single field of vision area.

14. An anesthesia system in accordance with claim 9, wherein:
the anesthetic dispenser further comprises an adjusting handwheel for adjusting a quantity of anesthetic fed by the anesthetic dispenser, and indica on the adjusting handwheel that changes relative to the single field of vision area with a change in an adjustment position and defines the another image pattern at the anesthetic dispenser.

15. An anesthesia system in accordance with claim 14, wherein:
the anesthetic dispenser includes an anesthetic filling level indicator fixed to the anesthesia apparatus, the anesthetic filling level indicator comprising an external coupling window;
the dispenser interface unit further comprises a further image pattern at the anesthetic dispenser, that changes during operation of the anesthesia system and presents data relating to a current state of the anesthetic dispenser, the further image pattern comprising the external coupling window; and
the further image pattern is in the single field of vision area.

16. An anesthesia system in accordance with claim 15, wherein the anesthetic filling level detector indicates a filling level by changing a reflected radiation intensity with the reflected radiation intensity at the external coupling window changing in case of different filling levels, wherein the image pattern changes during operation of the anesthesia at least based on a change between the different filling levels.

17. An anesthesia system comprising:
an anesthesia apparatus;
a pneumatic interface;
an anesthetic dispenser with anesthetic, the anesthetic dispenser being connected to and disconnectable from the anesthesia apparatus with a pneumatic connection between the anesthesia apparatus and the anesthetic dispenser provided by the pneumatic interface and with no electric connection between the anesthesia apparatus and the anesthetic dispenser and no electric connection to the anesthetic dispenser;
a camera fixed to the anesthesia apparatus, the camera having a single two dimensional field of vision area directed at the anesthetic dispenser;
an image providing a code presenting at least one of anesthetic dispenser type data, anesthetic dispenser part number data, anesthetic dispenser serial number data and type of anesthetic in the anesthetic dispenser data; and
an anesthetic filling level indicator fixed to the anesthesia apparatus, the anesthetic filling level indicator comprising an external coupling window defining another image pattern at the anesthetic dispenser, the another image pattern changing during operation of the anesthesia system and presenting data relating to a current state of the anesthetic dispenser wherein the image pattern and the another image pattern are in the single field of vision area.

18. An anesthesia system in accordance with claim 17, wherein:
the anesthetic dispenser further comprises an adjusting handwheel for adjusting a quantity of anesthetic fed by the anesthetic dispenser;

the dispenser interface unit further comprises a further image pattern at the anesthetic dispenser, that changes during operation of the anesthesia system and presents data relating to a current state of the anesthetic dispenser, the further image pattern comprising indica on the adjusting handwheel that changes position relative to the single field of vision area with a change in an adjustment position; and the further image pattern is in the single field of vision area.

19. An anesthesia system in accordance with claim 18, further comprising a radiation source emitting at least one of infrared radiation, visible light and UV radiation at the image pattern and the another image pattern and directed at the image, the another image and the further image, wherein:

the camera operates in at least one of a visible spectral range, infrared range and UV range in coordination with the radiation source; and the anesthetic filling level detector indicates a filling level by changing a reflected radiation intensity with the reflected radiation intensity at the external coupling window changing in case of different filling levels, wherein the image pattern changes during operation of the anesthesia at least based on a change between the different filling levels.

* * * * *